United States Patent
Paul

(10) Patent No.: US 9,700,231 B2
(45) Date of Patent: Jul. 11, 2017

(54) HOLDER FOR DOUBLE LOOP COIL FOR MCP IMAGES

(71) Applicant: Dominik Paul, Bubenreuth (DE)

(72) Inventor: Dominik Paul, Bubenreuth (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/754,514

(22) Filed: Jan. 30, 2013

(65) Prior Publication Data

US 2013/0197352 A1    Aug. 1, 2013

(30) Foreign Application Priority Data

Jan. 31, 2012 (DE) .................. 10 2012 201 370

(51) Int. Cl.
| | | |
|---|---|---|
| *A61B 5/05* | (2006.01) | |
| *A61B 5/055* | (2006.01) | |
| *A61B 5/00* | (2006.01) | |
| *G01R 33/34* | (2006.01) | |

(52) U.S. Cl.
CPC ............ *A61B 5/055* (2013.01); *A61B 5/0555* (2013.01); *A61B 5/6825* (2013.01); *G01R 33/34007* (2013.01); *G01R 33/34046* (2013.01)

(58) Field of Classification Search
CPC  G01R 33/341; G01R 33/44; G01R 33/34007; G01R 33/34046; G01R 33/34084; G01R 33/34092; A61B 5/055; G01N 24/08
USPC ............................ 600/407–430; 324/318–322
See application file for complete search history.

(56) References Cited

U.S. PATENT DOCUMENTS

| | | | |
|---|---|---|---|
| 5,274,332 A * | 12/1993 | Jaskolski | G01R 33/34007 324/318 |
| 5,329,234 A | 7/1994 | Burton | |
| 5,361,764 A | 11/1994 | Reynolds et al. | |
| 5,427,103 A * | 6/1995 | Fujio | A61B 1/0051 600/101 |
| 5,502,387 A | 3/1996 | McGill | |
| 5,664,568 A * | 9/1997 | Srinivasan | G01R 33/3657 324/318 |
| 5,783,943 A * | 7/1998 | Mastandrea, Jr. | G01R 33/385 324/318 |
| 5,864,234 A * | 1/1999 | Ludeke | G01R 33/3415 324/307 |

(Continued)

FOREIGN PATENT DOCUMENTS

| | | |
|---|---|---|
| DE | 103 14 215 B4 | 11/2006 |
| JP | 2009254702 A | 11/2009 |

OTHER PUBLICATIONS

German Office Action dated Oct. 15, 2012, for corresponding German Patent Application No. DE 10 2012 201 370.9 with English translation.

(Continued)

*Primary Examiner* — Sanjay Cattungal
(74) *Attorney, Agent, or Firm* — Lempia Summerfield Katz LLC

(57) ABSTRACT

A holder for a local coil for an imaging system such as a magnetic resonance tomography (MRT) hand coil holder is provided. The MRT hand coil holder has recesses in side parts of the holder. A hand of a patient may be positioned between the side parts. The recesses in the side parts of the holder are each configured to accommodate at least one local coil.

18 Claims, 4 Drawing Sheets

(56) References Cited

U.S. PATENT DOCUMENTS

| | | | | |
|---|---|---|---|---|
| 5,929,639 | A * | 7/1999 | Doty | G01R 33/34069 324/309 |
| 5,952,830 | A * | 9/1999 | Petropoulos | G01R 33/385 324/318 |
| 6,023,166 | A * | 2/2000 | Eydelman | G01R 33/34053 324/318 |
| 6,144,203 | A * | 11/2000 | Richard | G01R 33/34053 324/318 |
| 6,499,484 | B1 | 12/2002 | Salminen | |
| 6,577,888 | B1 * | 6/2003 | Chan | G01R 33/3415 324/318 |
| 6,591,128 | B1 * | 7/2003 | Wu | G01R 33/34084 324/318 |
| 6,636,040 | B1 * | 10/2003 | Eydelman | G01R 33/34053 324/318 |
| 6,727,698 | B1 * | 4/2004 | Eydelman | G01R 33/34053 324/318 |
| 6,847,210 | B1 * | 1/2005 | Eydelman | G01R 33/341 324/318 |
| 7,221,160 | B2 * | 5/2007 | Leussler | G01R 33/3415 324/318 |
| 7,701,209 | B1 * | 4/2010 | Green | G01R 33/307 324/307 |
| 7,728,592 | B2 * | 6/2010 | Ma et al. | 324/318 |
| 2004/0251902 | A1 * | 12/2004 | Takagi | G01R 33/3456 324/318 |
| 2005/0127914 | A1 | 6/2005 | Eberler et al. | |
| 2006/0173390 | A1 * | 8/2006 | Van Wyk | A61B 6/0421 602/6 |
| 2006/0244448 | A1 * | 11/2006 | Ballon | G01R 33/34046 324/318 |
| 2007/0152667 | A1 * | 7/2007 | Schubert | G01R 33/34046 324/318 |
| 2008/0129298 | A1 * | 6/2008 | Vaughan | G01R 33/583 324/322 |
| 2010/0066367 | A1 * | 3/2010 | Ma | G01R 33/307 324/318 |
| 2010/0066368 | A1 * | 3/2010 | Gao | G01R 33/307 324/318 |
| 2011/0037470 | A1 * | 2/2011 | Driemel | G01R 33/36 324/318 |
| 2011/0040174 | A1 * | 2/2011 | Driemel | G01R 33/34007 600/422 |
| 2011/0210735 | A1 * | 9/2011 | Trakic | G01R 33/5659 324/309 |
| 2012/0153956 | A1 * | 6/2012 | Driemel | G01R 33/34007 324/322 |

OTHER PUBLICATIONS

Chinese office Action for related Chinese Application No. 2013 100 376 25.0 dated Sep. 1, 2016, with English Translation.

Korean Notice of Allowance for related Korean Application No. 10-2013-0010339, dated Jun. 24, 2016 with English Translation.

* cited by examiner

US 9,700,231 B2

HOLDER FOR DOUBLE LOOP COIL FOR MCP IMAGES

This application claims the benefit of DE 10 2012 201 370.9, filed on Jan. 31, 2012, which is hereby incorporated by reference.

BACKGROUND

The present embodiments relate to a holder for local coils.

Magnetic resonance devices (MRTs) for examining objects or patients using magnetic resonance tomography are known, for example, from DE10314215B4.

SUMMARY AND DESCRIPTION

The present embodiments may obviate one or more of the drawbacks or limitations in the related art. For example, a local coil is optimized for imaging a hand.

An embodiment of a holder for loop coils or ring-type coils for rheumatism examinations, for example, allow simple support of a hand between two loop coils in a manner that is different from other solutions.

DETAILED DESCRIPTION OF THE DRAWINGS

Figure 4:
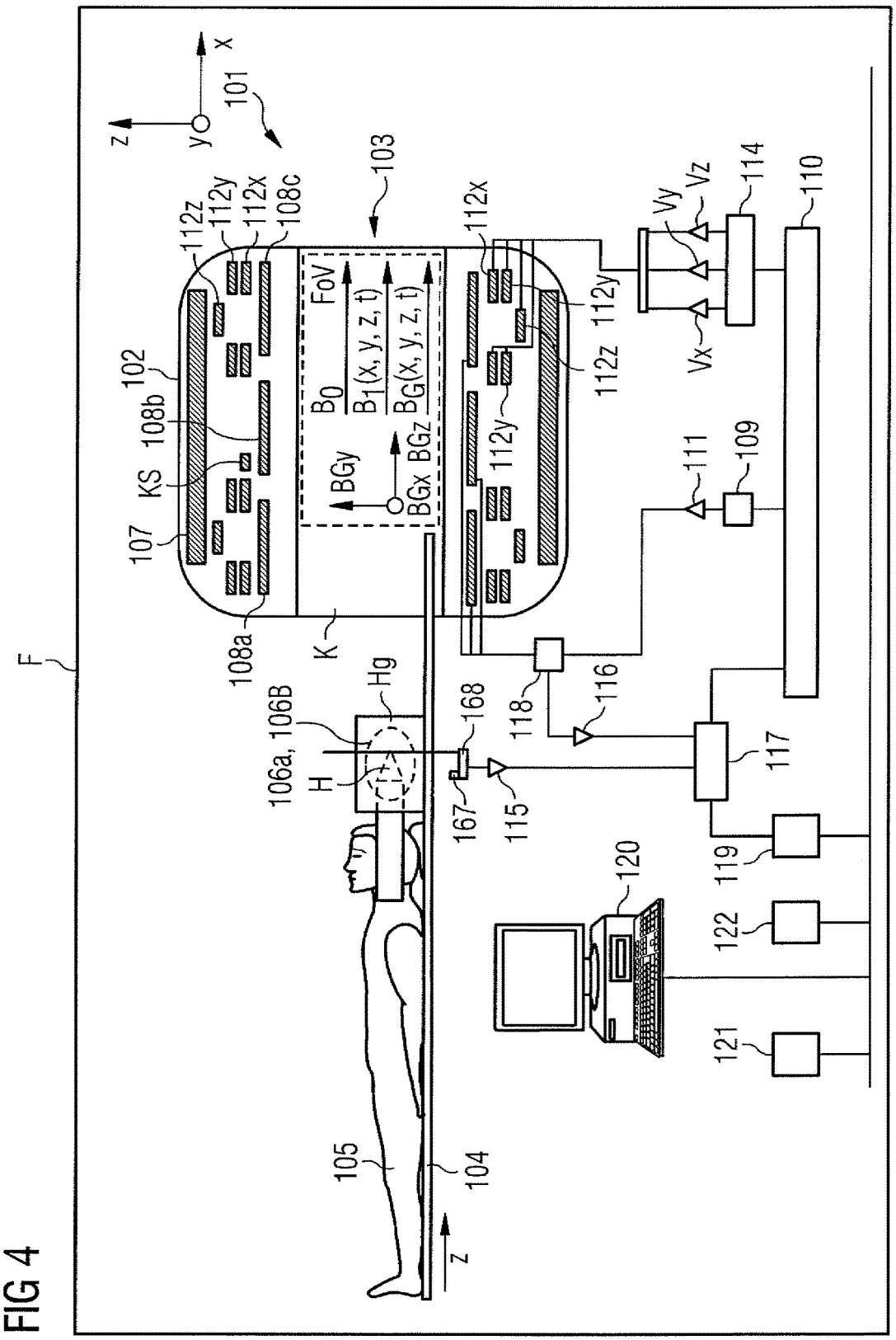
FIG. 4 shows a schematic diagram of one embodiment of a magnetic resonance tomography (MRT) system.

FIG. 4 shows one embodiment of an imaging magnetic resonance device MRT 101 (e.g., in a shielded room or Faraday cage F) having a whole body coil 102 with, for example, a tubular space 103, into which a patient couch 104 supporting a body (e.g., of an examination object such as a patient) 105 may be moved (e.g., with or without local coil arrangement 106) in the direction of the arrow z to generate images of, for example, the hand H (e.g., may also be positioned at a side of the body) of the patient 105 using an imaging procedure. Disposed on the patient, for example, is a local coil arrangement 106 (e.g., with individual coils 106 A, 106B) that may be used in a local region (e.g., a field of view (FOV)) of the MRT to generate images of a subregion of the body 105 in the FOV. Signals from the local coil arrangement 106 may be evaluated (e.g., converted to images, stored or displayed) by an evaluation device (e.g., including elements 168, 115, 117, 119, 120, 121) of the MRT 101 that may be connected, for example, by way of coaxial cable or radio (e.g., 167) to the local coil arrangement 106.

In order to use a magnetic resonance device MRT 101 to examine a body 105 (e.g., an examination object or patient) using magnetic resonance imaging, different magnetic fields, the temporal and spatial characteristics of which are matched as closely as possible to one another, are radiated onto the body 105. A powerful magnet (e.g., a cryomagnet 107) in a measuring cabin with, for example, a tunnel-type opening 103, generates a static powerful main magnetic field $B_0$ of, for example, 0.2 Tesla to 3 Tesla or even more. The body 105 to be examined, supported on a patient couch 104, is moved into a roughly homogeneous region of the main magnetic field $B_0$ in the FOV. Atomic spins of atomic nuclei of the body 105 are excited by way of magnetic high-frequency excitation pulses B1(x, y, z, t) that are radiated by way of a high-frequency antenna (and/or optionally, a local coil arrangement) shown in a highly simplified manner as a body coil 108 (e.g., a multipart coil 108a, 108b, 108c). High-frequency excitation pulses are generated, for example, by a pulse generation unit 109 that is controlled by a pulse sequence control unit 110. After amplification by a high-frequency amplifier 111, the high-frequency excitation pulses are conducted to the high-frequency antenna 108. The high-frequency system illustrated is only shown schematically. In other embodiments, more than one pulse generation unit 109, more than one high-frequency amplifier 111, and a number of high-frequency antennas 108a, b, c are used in a magnetic resonance device 101.

The magnetic resonance device 101 also has gradient coils 112x, 112y, 112z that are used during a measurement to radiate magnetic gradient fields for selective slice excitation and spatial encoding of the measurement signal. The gradient coils 112x, 112y, 112z are controlled by a gradient coil control unit 114 that, like the pulse generation unit 109, is connected to the pulse sequence control unit 110.

Signals emitted by the excited nuclear spins (e.g., of the atomic nuclei in the examination object) are received by the body coil 108 and/or at least one local coil arrangement 106, amplified by assigned high-frequency preamplifiers 116 and further processed and digitized by a receive unit 117. The recorded measurement data is digitized and stored as complex numerical values in a k-space matrix. A multidimensional Fourier transform may be used to reconstruct an associated MR image from the value-populated k-space matrix.

For a coil that may be operated in both transmit and receive mode (e.g., the body coil 108 or a local coil 106), correct signal forwarding is regulated by an upstream duplexer 118.

An image processing unit 119 uses the measurement data to generate an image that is displayed to a user by way of an operating console 120 and/or stored in a memory unit 121. A central computer unit 122 controls the individual system components.

In MR tomography, images with a high signal-to-noise ratio (SNR) are currently recorded using local coil arrangements (e.g., coils, local coils). These are antenna systems that are positioned in direct proximity on (anterior), below (posterior), next to, or in the body 105. During a measurement, the excited nuclei induce a voltage in the individual antennas of the local coil. The induced voltage is then amplified using a low-noise preamplifier (e.g., LNA, preamp) and forwarded to the electronic receive system. High-field systems (e.g., 1.5T-12T or more) are used to improve the signal-to-noise ratio, even with high-resolution images. If more individual antennas may be connected to an MR receive system than there are receivers present, a switching matrix (e.g., RCCS), for example, is incorporated between receive antennas and receivers. This routes the currently active receive channels (e.g., the receive channels in the FOV of the magnet at the time) to the receivers present. This allows more coil elements to be connected than there are receivers present, since for whole body coverage, only the coils present in the FOV or in the homogeneity volume of the magnet are to be read out.

A local coil arrangement 106 may, for example, be an antenna system that may include, for example, one or, in the case of an array coil, a number of antenna elements (e.g., coil elements). These individual antenna elements are embodied, for example, as loop antennas (e.g., loops), butterfly coils, flex coils or saddle coils. A local coil arrangement includes, for example, coil elements, a preamplifier, further electronic elements (e.g., baluns), a housing, bearings and may include a cable with plug that is used to connect the local coil arrangement to the MRT system. A receiver 168 on the system side filters and digitizes a signal received from a local coil 106 (e.g., by radio) and transfers the data to a digital signal processing device that may derive an image or spectrum from the data obtained by measurement and make the image or spectrum available to the user (e.g., for subsequent diagnosis by the user and/or storage).

Figure 3:
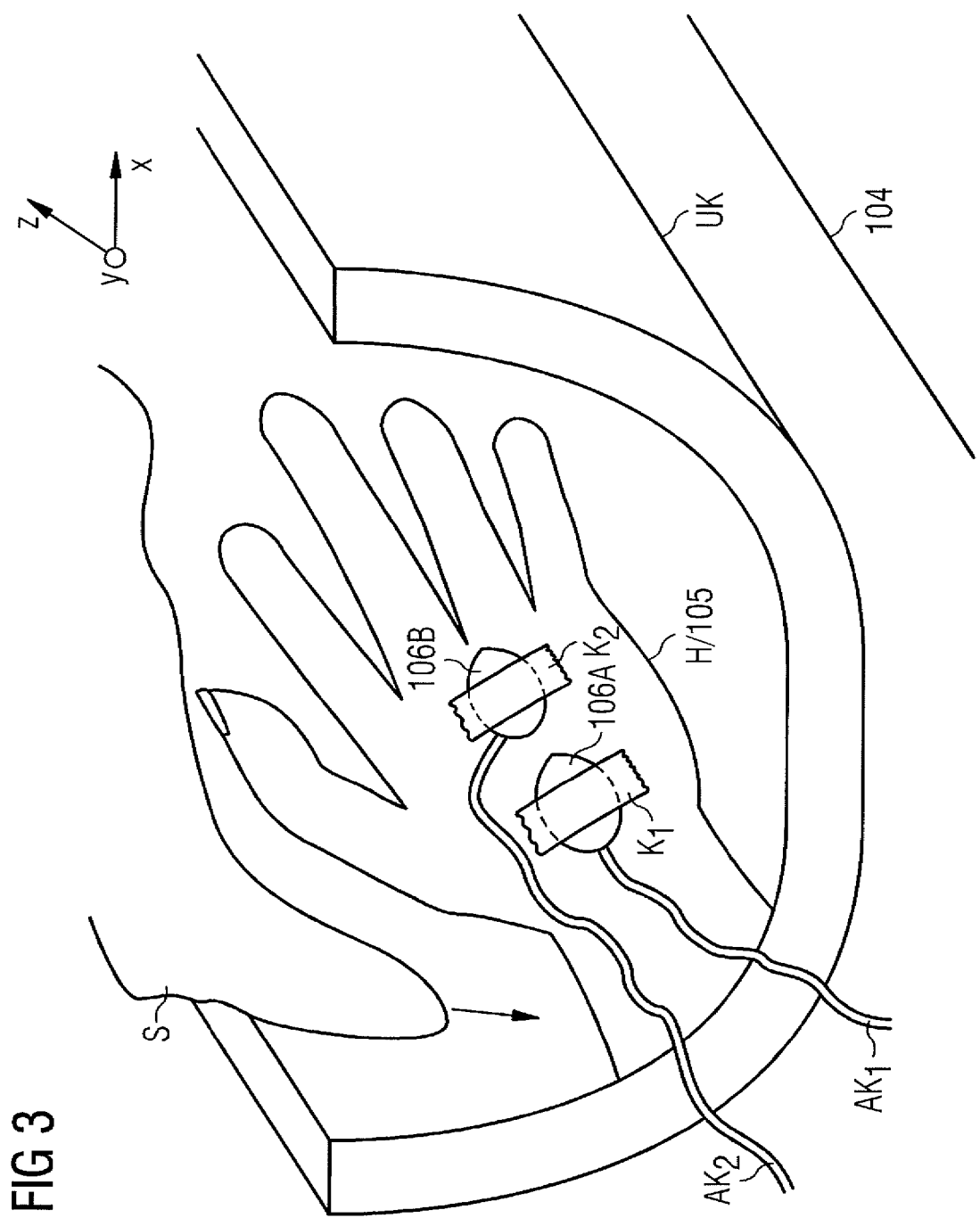
FIG. 3 shows a variant for positioning local coils on a hand.

As shown in FIG. 3, the positioning of the coils 106 A, 106 B according to a solution provides that the coils (or antennas) 106A, 106B are positioned individually inside the hand and/or on the surface of the hand H of the patient 105 and fixed to the hand H with medical adhesive tape K1, K2. The hand H is supported on a patient table 104. A longish cushion UK with a U-shaped cross section is provided as a support aid, as also for foot/ankle examinations. The hand H is weighed down with a beanbag S, and the entire arrangement is fixed in place with Velcro tape, for example, around the beanbag S and the U-shaped cushion UK. This is to prevent or reduce movement during imaging.

The coils 106A, 106B (e.g., MRT local) are connected via long adapter cables to the table 104 (e.g., interfaces in the table), making handling even more problematic and only allowing a single hand position. As a result, the support for the patient as a whole is to be adapted for this position. In some instances, two people are required to position the coils and support the patient appropriately. The adapter cables prevent free movement of the coils, so that freedom of movement is severely restricted while the coils are being positioned. If the adapter cables are not connected, the adapter cables may drop from the table and displace the arrangement due to the weight of the adapter cables.

Figure 1:
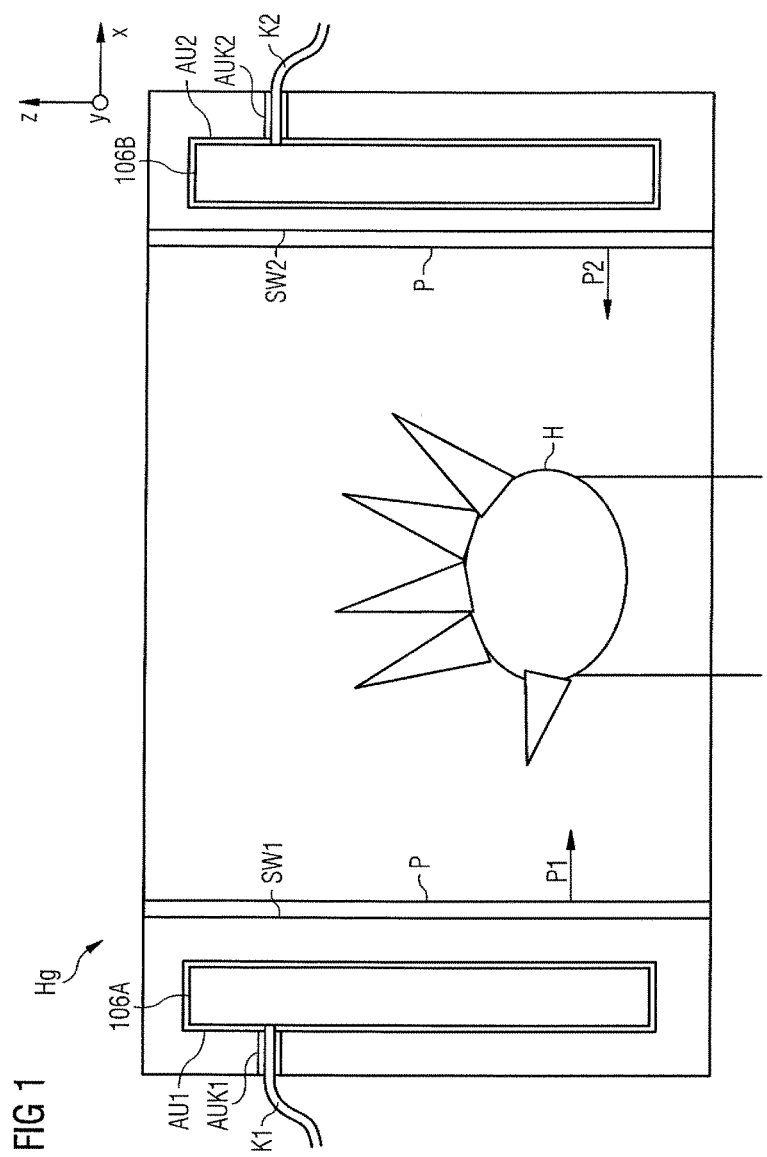
FIG. 1 shows a plan view of one embodiment of a holder for local coils for imaging a hand.
Figure 2:
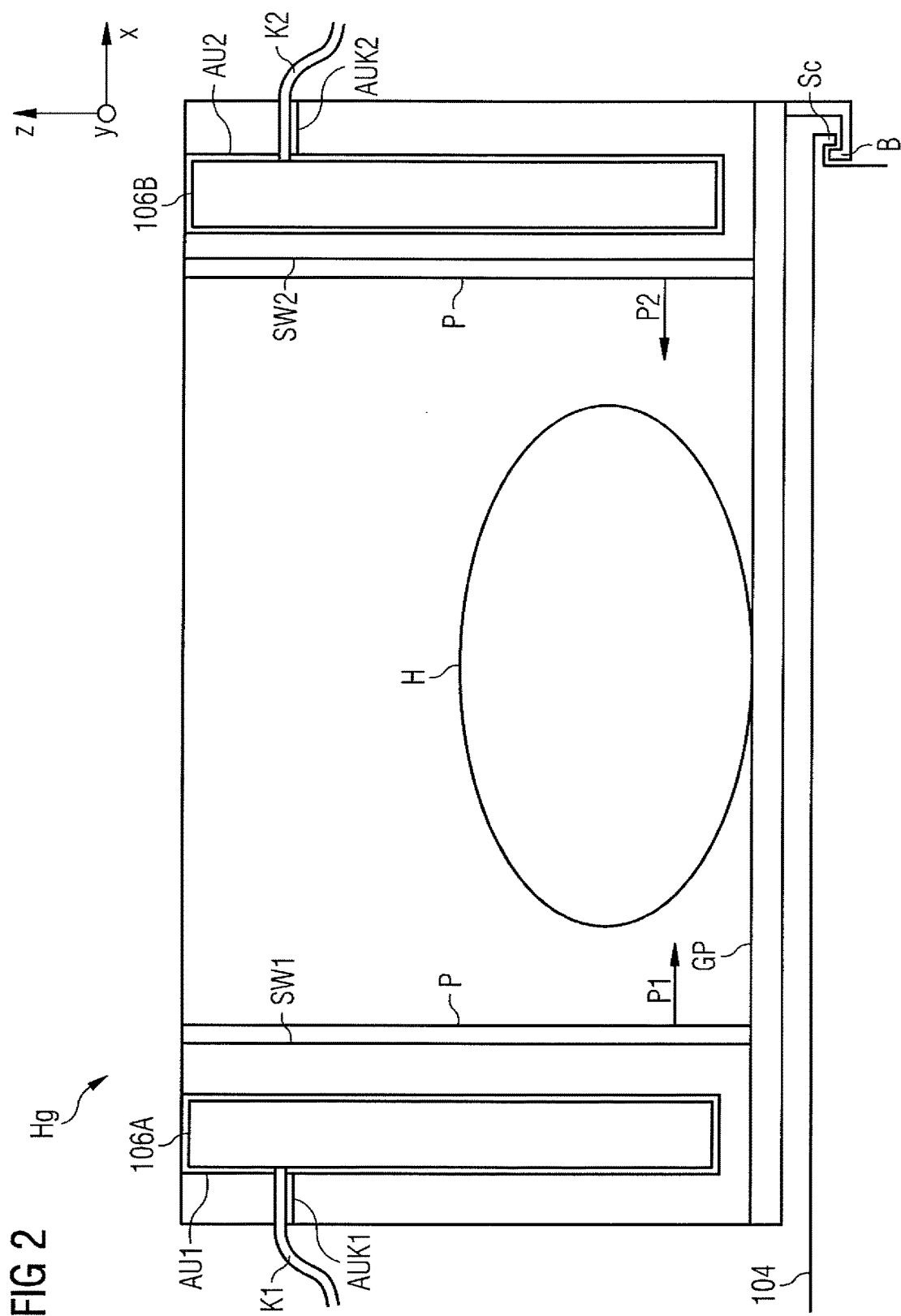
FIG. 2 shows a cross section of one embodiment of a holder for local coils for imaging a hand.

FIGS. 1 and 2 show an exemplary embodiment of a holder Hg for coils 106A, 106B for an MRT 101 for imaging a hand H.

One embodiment provides for a holder Hg that may be fastened in a fixed manner to a patient table 104 (e.g., with a fastening B in a lateral rail Sc.) and that has at least two recesses AU1, AU2 for the at least or just two loop coils 106A, 106B. One coil 106A, 106B may be inserted in a corresponding one of the recesses (e.g., with or without clearance in the recess or cutout). The recesses AU1, AU2 in the holder Hg are, but do not have to be, located on opposing sides (e.g., in FIGS. 1, 2, left and right) of the holder Hg (e.g., in a side wall SW1, SW 2, respectively, of the holder), so that the hand H of the patient 105 may easily be pushed in between. The coils 106A, 106B may be inserted into the recesses AU1, AU2, for example. The side walls and/or coils may be such that the side walls and/or coils may be displaced, for example, along a rail, in the direction of the arrows P1, P2 relative to the hand H and/or to the further side wall, respectively. The coils 106A, 106B may be "clipped," for example, into one of the recesses AU1, AU2. For example, the coils 106A, 106B may be fastened with latching strips of a coil 106A that engage in an elastic manner in latching recesses in a side wall SW1, for example, of the holder Hg, or with an elastically insertable pivot device.

Further recesses AUK1, AUK2 may be present to guide cables K1, K2 (e.g., for HF signals to be transmitted or received signals) from the coils 106A, 106B by way of contacts (e.g., on the couch 105; may be connected to an evaluation device) so that after a coil 106A has been positioned in the holder Hg in each instance, the holder Hg may have a flat surface without projecting elements. To allow adaptation to the patients 105 to be examined (e.g., whose hand thickness may vary greatly in patients such as rheumatism patients), at least one of the two side parts SW1, SW2 may be movable in an infinitely variable manner (e.g., in/counter to the direction of the other side part) to provide space and to facilitate the insertion of the hand. The side parts may be padded with padding P to allow the side parts to rest closely against the hand H to be examined in order to reduce the risk of movement and at the same time not to cause pain.

The two side parts SW1, SW2 may also have, for example, a closing mechanism or latching mechanism, so that the two side parts SW1, SW2 may be fixed in place during the examination.

The hand H may also be positioned between the side walls of the holder, rotated through 90 degrees about an axial longitudinal direction in relation to the diagram in FIGS. 1, 2 (e.g., with the thumb in the y-direction (upward in FIG. 2)).

A holder for loop coils for examining rheumatism patients, for example, may allow simple positioning and/or support of a hand between two loop coils.

Advantages can be simple handling, faster support or positioning of the patient ("simple hand insertion"), relatively little operator input, and relatively high level of patient comfort, as coils do not have to be bonded in place.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A holder for a local coil for an imaging system, the holder comprising:
   a base;
   side parts positioned on the base, between which a hand of a patient is positionable, wherein a first of the side parts is configured to slide relative to a second of the side parts, the second side part is configured to slide relative to the first side part, or the first side part and the second side part are configured to slide relative to each other, at least one of the first side part and the second side part being configured to slide in a direction parallel to the base, towards and away from the other of the first side part and the second side part; and
   a recess in each of the side parts,
   wherein each of the recesses is configured to accommodate at least one local coil.

2. The holder as claimed in claim 1, wherein the holder is a magnetic resonance tomography (MRT) hand coil holder.

3. The holder as claimed in claim 2, wherein the MRT hand coil holder is for MRT imaging of the hand.

4. The holder as claimed in claim 1, further comprising a fastening device for fastening the holder to a magnetic resonance tomography (MRT) patient table.

5. The holder as claimed in claim 1, wherein the recesses are located on opposing sides of the holder to allow the hand of the patient to be positioned in between.

6. The holder as claimed in claim 1, wherein the coils are insertable into the recesses.

7. The holder as claimed in claim 1, wherein the coils are insertable into one of the recesses.

8. The holder as claimed in claim 7, wherein the coils are insertable into the one recess with latching strips on one of the coils, the latching strips engaging in an elastic manner in latching recesses in one of the side parts.

9. The holder as claimed in claim 1, wherein the side parts include additional recesses for cables leading to the local coils.

10. The holder as claimed in claim 1, wherein one or both of the side parts are movable counter to a direction of movement of the other side part.

11. The holder as claimed in claim 1, wherein the side parts have padding.

12. The holder as claimed in claim 1, wherein the side parts have a closing mechanism, a latching mechanism, or a combination thereof to fix the side parts in place during an imaging examination.

13. The holder as claimed in claim 3, further comprising a fastening device for fastening the holder to a magnetic resonance tomography (MRT) patient table.

14. The holder as claimed in claim 3, wherein the recesses are located on opposing sides of the holder to allow the hand of the patient to be positioned in between.

15. The holder as claimed in claim 3, wherein the coils are inseratable into the recesses.

16. The holder as claimed in claim 3, wherein the coils are insertable into one of the recesses.

17. The holder as claimed in claim 16, wherein the coils are insertable into the one recess with latching strips on one of the coils, the latching strips engaging in an elastic manner in latching recesses in one of the side parts.

18. The holder as claimed in claim 3, wherein the side parts include additional recesses for cables leading to the local coils.

* * * * *